United States Patent [19]
Washburn et al.

[11] Patent Number: 5,719,137
[45] Date of Patent: Feb. 17, 1998

[54] METHOD OF PREVENTING NEURODEGENERATION AND COGNITIVE DYSFUNCTION USING 17α-DIHYDROEQUILENIN

[75] Inventors: Scott A. Washburn; Carol Ann Shively, both of Winston-Salem, N.C.

[73] Assignee: Wake Forest University, Winston-Salem, N.C.

[21] Appl. No.: 753,988

[22] Filed: Dec. 3, 1996

[51] Int. Cl.$^6$ .................................................. A61K 31/56
[52] U.S. Cl. ........................ 514/182; 514/178; 514/179
[58] Field of Search ................................ 514/182, 178, 514/179

[56] References Cited

U.S. PATENT DOCUMENTS

| | | | |
|---|---|---|---|
| 3,507,889 | 4/1970 | Marshall | 260/397.5 |
| 4,154,820 | 5/1979 | Simoons | 424/175 |
| 5,510,342 | 4/1996 | Washburn et al. | 514/179 |
| 5,545,635 | 8/1996 | Bryant et al. | 514/177 |

OTHER PUBLICATIONS

Effects of Estrogen On Memory Function In Surgically Menopausal Women; *Psychoneuroendocrinology*, vol. 17, No. 5, pp. 485–495, 1992.
Gonadal Steroids Regulate Dendritic Spine Density In Hippocampal Pyramidal Cells in Adulthood: *The Journal Of Neuroscience*, Apr. 1990. 10(4) : 1286–1291.
The Potential Role For Estrogen Replacement Therapy in the Treatment of the Congnitive Decline and Neurodegeneration Associated With Alzheimer's Disease *Neurogiology of Aging*, vol. 15, Suppl. 2, pp. S195–S197, 1994.
Premarin Intracenous, *Physicians' Desk Reference*, 1996 p. 2787.
The Saga of the Ring B Unsaturated Equine Estrogens *Endocrine Reviews*, 1988.
Hormone Therapy To Prevent Disease and Prolong Life in Posmenopausal Woman, *Annals of Internal Medicine*, vol. 117, No. 12, 15 Dec. 1992.
Association of Hormone–Replacement Therapy With Various Cardiovascular Risk Factors In Postmenopausal Women *The Journal of New England Medicine*, vol. 328, No. 15 Apr. 15, 1993, pp. 1069–1075.
Correlates of Postmenopausal Estrogen Use and Trends Through the 1980s in Two Southeastern New England Communities; *American Journal of Epidemiology*, vol. 137 No. 10, pp. 1125–1135, 1993.
Bleeding Patterns in Postmenopausal Women Taking Continuous combined or Sequential Regimens of Conjugated Estrogens With Medroxyprogesterone Adetate; *Obstetrics & Gynecology*, vol. 83, No. 5, Part 1, May 1994.
The Use of Estrogens and Progestins and the Risk of Breast Cancer in Postmenopausal Women; *The N.E. Journal Of Medicine*, vol. 332, No. 24, Jun. 15, 1995.
Reduced Mortality Associated With Long–Term Postmenpausal Estrogen Therapy; *Obstetrics & Gynecology*, vol. 87, No. 1 Jan. 1996.
A Conjugated Equine Estrogen with Differential Effects on Uterine Weight and Plasma Cholesterol in the Rat *Am. J. Obstet. Gynecol;* Aug. 1993, pp. 251–256.
Interaction of Ring B Unsaturated Estrogens with Estrogen Receptors of Human Endometrium and Rat *Uterus Steroids,* 1991, vol. 56, April pp. 201–210.
Premarin Components: Uterine, Cholesterol Lowering, and Bone Metabolic Effects, Jun. 1996 Endocrine Research, Lilly Research Laboratories.
Pharmacology of Conjugated Oestrogens; *Elsener Bio–Medical Press,* 1982 pp. 332–339.
Sex Hormones and Psychological Functioning in Post–Menopausal Women; *Experimental Gerontology,* vol. 29, Nos. 3/4, pp. 423–430 1994.
Effects of 17α–Dihydroequilenin Sulfate on Athero–Sclerotic Male and Female Rhesus Monkeys; *Am J. Obstet Gynecol;* Aug.1996, pp. 341–351.
Roles of Estradiol and Progesterone in Regulation of Hippocampal Dendritic Spine Density During the Estrous Cycle in the Rat; *Journal of Comparative Neurology,* 1993.
Evaluation of Equilin 3–Monosulfate and Other Estrogens *Arch Intern Med*/vol. 128, Aug. 1971.
The Metabolism of Equilin in Normal Men; *J.Steroid Biochem,* vol. 17, pp. 217–23, 1982.
Pharmacokinetics of Equilin and Equilin Sulfate in Normal women and Men; J. Clinical Endo. and Meta., 1983 vol. 56, No.5 1048–1056.
Pharmacokinetics of 17α–Dihydroequilin Sulfate and 17α–Dihydroequilin in Normal Postmenopausal Women; *Journal of Clinical Endocrinology and Metabolism,* vol. 78 No. 1, pp.197–204, 1994.

*Primary Examiner*—Theodore J. Criares
*Attorney, Agent, or Firm*—Rhodes, Coats & Bennett, L.L.P.

[57] ABSTRACT

A method of using a steroidal compound, 17α-dihydroequilenin, to prevent and treat neurodegeneration and cognitive dysfunction in estrogen deficient females and to reduce the risk of Alzheimer's related dementia and other senile dementia related conditions in both males and females. The method comprises administering 17α-dihydroequilenin in a therapeutically effective amount to a mammal in need of increased cognitive function or to a mammal susceptible to estrogen deficiency-related neurodegeneration or to senile dementia of the Alzheimer's type.

24 Claims, 1 Drawing Sheet

METHOD OF PREVENTING NEURODEGENERATION AND COGNITIVE DYSFUNCTION USING 17α-DIHYDROEQUILENIN

BACKGROUND OF THE INVENTION

The present invention relates to a method of using a steroidal compound to prevent the degeneration of neurons associated with cognitive functions like memory and attention in mammals. More particularly, the present invention relates to a method of using 17α-dihydroequilenin to prevent neurodegeneration and cognitive dysfunction in estrogen deficient females and to reduce the risk of Alzheimer's related dementia in both males and females.

Cessation of estrogen production by the ovaries in women, commonly known as menopause, is often accompanied by numerous physical and psychological changes. Prominent among the menopausal symptoms are changes in mood and sexual functioning as well as noticeable decrements in cognitive functions, particularly memory and attention. These changes are also apparent in women who exhibit ovarian deficiencies that are not attributable to menopause. Changes in the hormonal milieu during menopause are also responsible for postmenopausal osteoporosis, a condition characterized by large and rapid bone loss, which affects the majority of women over 60 years old in the United States. Further, postmenopausal women are one group of aging persons at increased risk for developing coronary heart disease.

Decrements in cognitive functioning, particularly memory and attention, have long been associated with menopause. The mammalian hippocampus has been shown to be involved in a number of important functions, inter alia, cognitive processes. Furthermore, neurons of the adult hippocampal formation appear to be especially sensitive to alterations in female sex hormone levels.

Various estrogen replacement therapies (ERTs) have been studied in an effort to understand the psychological changes that occur in menopausal women; however, these ERTs have serious drawbacks which will be discussed in greater detail hereinbelow. Phillips et al. discloses that estradiol treatment appears to ameliorate the deleterious changes in cognitive function in surgically menopausal women, but the mechanism is not yet understood [*Psychoneuroendocrinology* 17:485 (1992)].

In studying the hippocampus, a brain region critical to memory, Gould et al. found that the morphologic characteristics of hippocampal neurons were indeed affected by changes in the circulating levels of female sex hormones, and observed that removal of circulating gonadal steroids by ovariectomy of adult female rats resulted in a profound decrease in dendritic spine density in CA1 pyramidal cells of the hippocampus [*J. Neurosci.* 10:1286 (1990)]. Gould et al. further reported that short-term subcutaneous estradiol benzoate increased the spine density of apical dendrites of pyramidal cells in the CAI region of the hippocampus. Since dendritic spines are believed to represent postsynaptic sites, the observed increased spine density by Gould et al. may indicate an increase in synapses, suggesting a possible mechanism by which estradiol may positively effect cognitive function in this neural region. Neither the Phillips nor the Gould references suggested the use of 17α-dihydroequilenin as a hormonal therapeutic agent for effecting positive changes in cognitive function.

Neurodegeneration as well as severe cognitive impairment is also associated with Alzheimer's disease and other dementia related conditions. Although the mechanism of neuronal loss with Alzheimer's is still unknown, it has been reported that age-associated changes i.e., hormonal changes may contribute to the expression of this disease. In this regard, Simpkins et al. reported that ovarian factors are of great importance in the normal maintenance of brain function, and that the loss of ovarian steroids at menopause may play a key role in the cognitive decline and neurodegeneration that are associated with Alzheimer's disease [*Neurobiology of Aging* 12 (Supp. 2):s195 (1994)]. Simpkins et al. further found that when estrogen replacement therapy was administered to ovariectomized rats, in particular 17β-estradiol, the rats exhibited a superior retention of previously learned behavior. Acetylcholine uptake was also measured to compare the effects of ERT and the absence of ERT on cholinergic neurons. Results indicated that estrogen loss was the critical hormonal event effecting cholinergic neuronal activity.

Conjugated equine estrogens such as Premarin® (Wyeth-Ayerst Laboratories, Princeton, N.J.) are commonly used in an ERT regimen as the primary treatment for menopausal, postmenopausal and estrogen deficiency related symptoms in women. An extract from pregnant mares' urine, Premarin® contains a mixture of ten different conjugated estrogens occurring as sodium salts, water-soluble estrogen sulfates blended to represent the average composition of material derived from the pregnant mares' urine. Premarin® contains estrone, equilin and 17α-dihydroequilenin, together with trace amounts of 17α-estradiol, equilenin, and 17α-dihydroequilenin as salts of sulfate esters. 17α-dihydroequilenin sulfate comprises approximately 1–2% of the total steroidal content of Premarin®, and is actually classified as an impurity in Premarin® in the United States Pharmacopoeia. It is also recognized in the art that the biological effects of Premarin® are the sum of the effects of its various components [see, e.g., Bhavnani, V. R., *Endocrine Reviews*, 9(4):396–416, 406 (1988)].

It is well-known to those skilled in the art related to ERTs that tissue specificity differs with each estrogen, so that the physiological effects that one estrogen has on a particular tissue do not predict the effects for other estrogens. While estradiol and conjugated equine estrogens exhibit certain beneficial effects and appear to reduce cardiovascular disease and increase bone density in menopausal women [Grady, D. et al., *Ann. Intern. Med.* 117:1016 (1992)], a number of uterine side effects associated with both hormonal treatments make these estrogens significantly less appealing for long-term use. In fact, as a result of the following side effects with these hormonal treatments, few eligible menopausal women take long-term hormone replacement therapy [Nabulsi, A. A. et al. *N. Engl. J. Med.* 328:1069 (1993); Derby, C. A. et al. *Am. J. Epidemiol.* 137:1125 (1993)]. More specifically, an increased risk of endometrial carcinoma has been clearly established with the use of these treatments unless they are administered concomitantly with a sufficient dose of progestin. Unfortunately, endometrial protection against carcinoma does not prevent unwanted side effects such as vaginal bleeding, and most women will experience unexpected and frightening vaginal bleeding during the first year of ERT despite following regimens designed to induce amenorrhea. Progestins also have been implicated in increasing the risk of breast cancer in women as compared to both non-users and women who take unopposed estrogens [Archer, D. M. et al., *Am. J. Obstet. Gynecol.* 173:471 (1995); Stampfer, M. J. et al., *N. Engl. J. Med.* 332:1589 (1995); Ettinger, B. et al., *Obstet. Gynecol.*, 87:6 (1996)].

It is also well accepted that estrone (a metabolically active metabolite of 17β-estradiol) causes a thickening of the uterine lining as well as increases uterine weight by about 8–10 fold [Washburn, S. A. et al., *Am. J. Obstet. Gynecol.* 169:251 (1993)]. Although large doses (10 µg administered by sub-cutaneous injection daily which is equivalent to approximately 3.25 g in women) of estradiol have been shown to influence the morphology of hippocampal neurons in the adult rat as reported by Gould et al., these doses are much higher than the standard menopause hormone therapy doses (1.0 mg estradiol administered daily and orally or 0.625 mg Premarin® administered orally and daily) that are currently used for women, and would result in heavy and intolerable uterine bleeding and greatly increase the risk of endometrial cancer.

Currently, there are no estrogen therapies with beneficial effects on the central nervous system as well as the cardiovascular and skeletal systems without trophic effects in the endometrium. There, thus, remains a need for an alternative estrogen therapy with beneficial effects on the central nervous system without uterotrophic effects.

SUMMARY OF THE INVENTION

The present invention is directed to the use of 17α-dihydroequilenin, a steroidal compound, to prevent neurodegeneration associated with cognitive dysfunction in female mammals exhibiting estrogen deficiency conditions and/or diseases including menopause. The present invention additionally provides a method of using 17α-dihydroequilenin to reduce the risk of Alzheimer's disease and other dementia related conditions in both males and females. The present invention further provides a method of using 17α-dihydroequilenin for the treatment of the above conditions and/or diseases by administering a therapeutically effective amount of 17α-dihydroequilenin or a mammalian metabolic conjugate thereof and an appropriate pharmaceutical carrier.

In preventing degeneration of neurons associated with cognitive functions like memory and attention, 17α-dihydro-equilenin is administered in therapeutically effective amounts to mammals susceptible to estrogen deficiency conditions and/or diseases including, but not limited to, those mammals with chemical castration from chemotherapy, anorexia/bulimia, hypogonadism, etc. Similarly, mammals susceptible to Alzheimer's type senile dementia or other senile dementia type conditions and/or diseases are administered 17α-dihydro-equilenin in therapeutically effective amounts as a prophylaxis. Other groups of mammals that are susceptible to the risk of developing neurodegeneration and cognitive dysfunction will be apparent to those skilled in the art.

The term "therapeutically effective amount" as used in the present invention is defined as the dose which provides effective treatment or prevention of the above described conditions and/or diseases to mammals, in particular humans.

The use of 17α-dihydroequilenin to prevent and/or treat neurodegeneration associated with cognitive dysfunction in estrogen deficient mammals and to reduce the risk of senile dementia of the Alzheimer's type provides distinct advantages over traditional estrogen replacement therapies. 17α-dihydroequilenin has demonstrated beneficial effects on the central nervous system function without uterotrophic effects of the type associated with estradiol. In contrast to other estrogens like estradiol which are known to cause a thickening of the uterine lining and increase uterine weight, studies have shown that 17α-dihydroequilenin has minimal to no estrogenic activity in the uterus or the hypothalamic pituitary portions of the gonadal axis as determined with the following traditional measures of estrogenic potency: 1) by relative binding affinity to the human endometrial and rat uterine cytosol and nuclear estradiol receptors; 2) the Allen-Doisy test (the amount of a particular estrogen needed to double the weight of a rat uterus); 3) by its uterotrophic potency; and 4) its inability to suppress urinary gonadotropin levels in oophorectomized women [Stern, Michael, *Maturitas*, 4:333 (1982); Howard et al., *Arch. Int. Med.*, 128:229 (1971)].

Additionally, one of the co-inventors of the present invention has demonstrated that 17α-dihydroequilenin reduces plasma cholesterol in rats and improves coronary artery vasomotor function in macaques at doses that have no apparent uterotrophic effects [see U.S. Pat. No. 5,510,342 and Washburn, S. A. et al., *Am. J. Obstet. Gynecol.* 175:341 (1996)]. Unlike other ERT's like estradiol which require concomitant administration with a sufficient dose of progestin to avoid vaginal bleeding and reduce the risk of endometrial carcinoma, 17α-dihydroequilenin may be administered by itself as a single hormonal therapeutic agent without the risk of endometrial cancer.

In the present invention, 17α-dihydroequilenin prevents atrophy of hippocampal CA-1 pyramidal cell apical dendritic spines, a brain region critical for memory and attention. While estradiol has been shown to exert a similar effect in rats, the doses for estradiol were much higher than those currently used for standard menopause hormone therapy, and would result in heavy and intolerable uterine bleeding and greatly increase the user's risk of endometrial cancer.

The mammalian metabolic conjugates used in the present invention are sulfates and glucuronides of 17α-dihydroequilenin. 17α-dihydroequilenin can be used either in the form of a mono- or di-conjugate. It is further contemplated that any derivative of 17α-dihydroequilenin that forms 17α-dihydroequilenin or conjugate thereof in vivo may be used in treating or preventing the conditions and/or diseases described hereinabove.

In one aspect of the present invention, a method is disclosed for preventing estrogen deficiency related neurodegeneration and cognitive dysfunction in a mammal, comprising administering to a mammal susceptible to estrogen deficiency related neurodegeneration a therapeutically effective amount of 17α-dihydroequilenin or mammalian metabolic conjugate thereof.

In another aspect of the present invention, the route of administration for 17α-dihydroequilenin is selected from the group consisting of oral, intravenous, parental, transdermal, rectal, intravaginal, intranasal, and intrabronchial administration.

In yet another aspect of the present invention, the mammal susceptible to estrogen deficiency related neurodegeneration is a post-menopausal female. However, other medical conditions where estrogen deficiency may occur include, but are not limited to, natural or surgical menopause, chemical castration (from chemotherapy), anorexia/bulimia, hypogonadism from over exercising, mental stress, genetic absence of ovarian tissue, etc.

In yet another aspect of the present invention, 17α-dihydroequilenin or mammalian metabolic conjugate thereof is used to treat an estrogen deficient mammal in need of increased cognitive function.

In another aspect of the present invention, a method is disclosed for preventing neurodegeneration and cognitive dysfunction associated with Alzheimer's disease and other dementia related disorders, comprising administering to a mammal susceptible to neurodegeneration associated with dementia disorders a therapeutically effective amount of 17α-dihydroequilenin or mammalian metabolic conjugate thereof.

The preceding and further objects of the present invention will be appreciated by those of ordinary skill in the art from a reading of the detailed description of the preferred embodiments which follow, such description being merely illustrative of the present invention.

BRIEF DESCRIPTION OF THE DRAWING

The invention will be better understood after a reading of the following description of the preferred embodiments when considered with the drawing.

DESCRIPTION OF THE PREFERRED EMBODIMENTS

Figure 1:
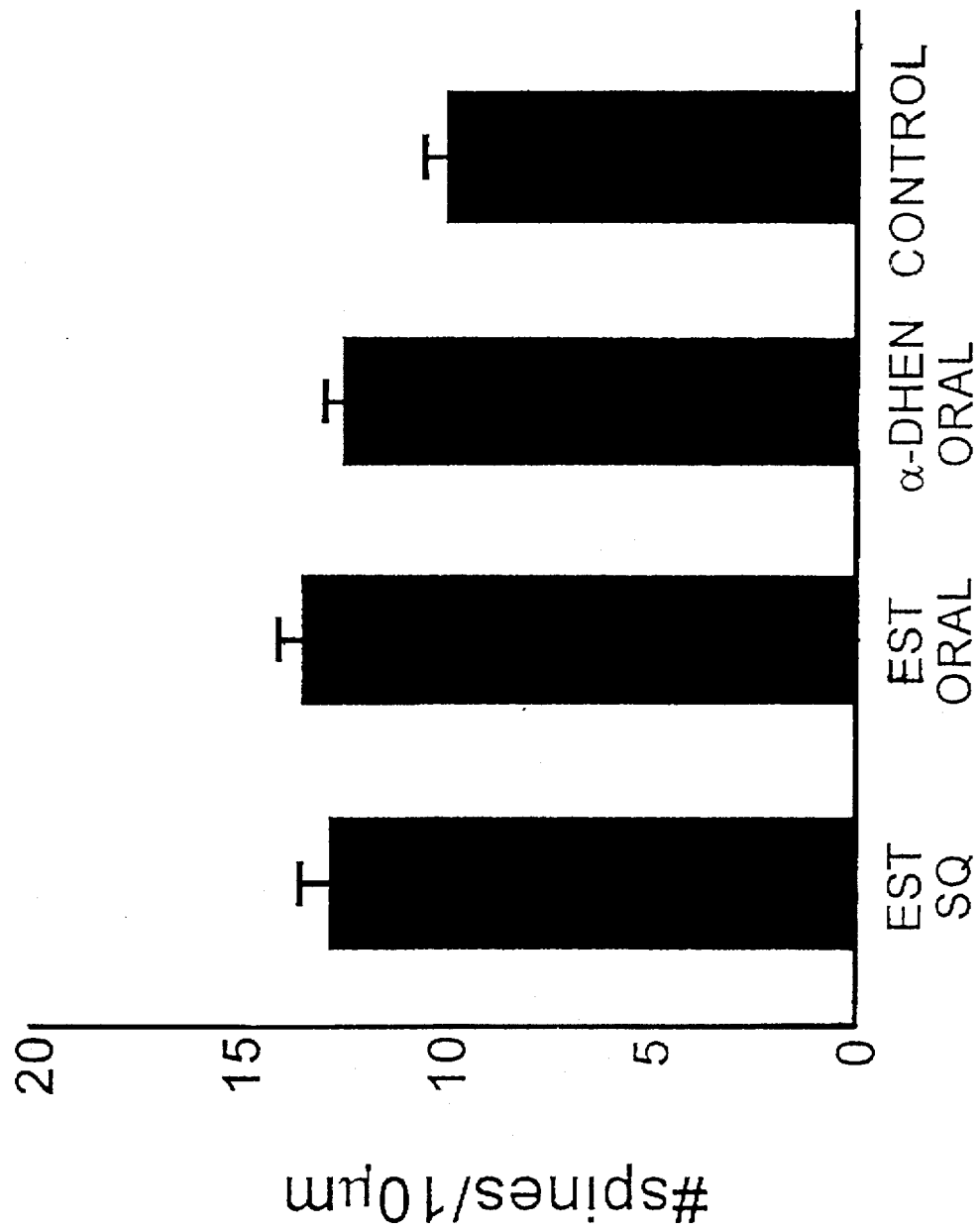
FIG. 1 illustrates the apical dendrite spine density (mean ±SEM) of pyramidal cells from the CA1 region of the hippocampus expressed as the number of spines per 10 μm of dendrite in ovariectomized rats (n=4 brains/group). EST= estradiol; SQ=subcutaneous; αDHEN=17α-dihydroequilenin.

In the studies of the present invention using ovariectomized rats, the effects of short-term (2 to 3 days) oral 17β-estradiol, subcutaneous estradiol benzoate, and oral 17α-dihydroequilenin treatment were compared versus untreated controls on the apical dendrite spine density of pyramidal cells of the CA1 region of the hippocampus (n=4 brains/group). All three treatments resulted in increased spine densities relative to untreated controls, and there were no apparent differences between the treatments. These results suggest that 17α-dihydroequilenin is a prime candidate for a single-agent hormone replacement therapy to treat mammals with an estrogen deficiency condition such as menopause as well as to reduce the chronic disease risk of Alzheimer's dementia or other dementia related conditions in both males and females.

EXAMPLE 1

Materials

17α-dihydroequilenin is commercially available and the conjugates are either commercially available or can be prepared using standard chemical methodology.

Test subjects were 51 retired breeder female Sprague-Dawley rats (10 months of age, ranging from 220 to 270 g body weight) matched for birth month. The rats were housed in single cages and exposed to 12-hour light/dark cycles in a temperature- and humidity-controlled room. The animals were acclimatized to the semi-purified diet (see below for details) for 2 weeks. They were then anesthetized (ketamine hydrochloride 50 mg/kg and xylazine 10 mg/kg intraperitoneally) and ovariectomized. The rats began treatment 72 hours after ovariectomy. All procedures involving animals were approved by the Bowman Gray School of Medicine Animal Care and Use Committee.

EXAMPLE 2

Experimental Procedures

The ovariectomized rats were assigned to one of four treatment groups matched for body weight: 1) A control group (n=13) injected with 0.1 ml corn oil subcutaneously once/day for two days; 2) the estradiol benzoate group (n=13), given 10 μg in 0.1 ml sesame oil/rat/day subcutaneously for 2 days; 3) the micronized estradiol group (n=12), given 0.05 mg/day/rat of 17β-estradiol in the diet (see details below) for 3 days; and 4) the 17α-dihydroequilenin sulfate group (n=13), given 0.15 mg/day/rat of 17α-dihydroequilenin sulfate in the diet (see details below) for 3 days.

Micronized 171β-estradiol and 17∝-dihydroequilenin sulfate were added to a semi-synthetic diet containing approximately 40% of calories as fat and 0.08 mg/Cal cholesterol. A diet containing the hormones was fed as a 15-gram bolus each morning. After that portion was consumed, the rats were allowed ad libitum access to the diet without added hormone treatment for the duration of the day. Subcutaneous hormone and placebo injections were administered at the same time of day as the orally administered hormone treatments. All animals were given water ad libitum.

EXAMPLE 3

Necropsy and Tissue Preparation

At necropsy, the rats were deeply anesthetized with sodium pentobarbital (100 mg/kg injected intraperitoneally), the abdominal aorta clamped, and one half of the animals from each treatment group were transcardially perfused with 120 ml of 4% paraformaldehyde plus 1.5% picric acid (v/v) in 0.1M sodium phosphate buffer, pH 7.4. (Brains from the remaining animals in each group were processed differently for other assays.) Brains were then dissected from the cranial cavities, and postfixed at 4° C. in the perfusate overnight.

After postfixation, the brains were processed for Golgi impregnation using methods adapted for single-section staining [Woolley, C. et al., J. Comp. Neurol. 326:293 (1993)]. Briefly, the brains were blocked to include the rostral hippocampus, and 100 μm-thick sections were cut on a vibratome. Sections were allowed to fall into a bath of 3% potassium dichromate in distilled water, and were kept at room temperature overnight. The following day, sections were rinsed in distilled water, mounted onto ungelatinized slides, and a coverslip glued at each corner. Slide assemblies were incubated in darkness in 1.5% silver nitrate in distilled water for 2 days at room temperature. They were then dismantled, the sections rinsed in distilled water, dehydrated in graded ethanols, cleared in Americlear (Baxto Scientific, McGaw Park, Ill.), and coverslipped under Permount. Slides were coded to insure blinding of the treatment group during the analyses of dendritic spine density.

Pyramidal neurons in the CA1 region of the hippocampus were chosen for counting if they were relatively isolated for easy dendrite identification, sufficiently impregnated, and clearly visible. Dendrite branches to be counted were at least 2 mm in length and 20 mm or more from the cell body. A total of 713 segments were measured, and the average number of segments measured per rat was 44. The segments were traced (×1250) with a camera lucida drawing tube; all visible spines on the segment were counted, and the segment was measured using a Zeiss interactive digitizing analysis system.

The data were expressed as the number of spines per 10 μm. The mean number of spines/dendrite length (10 μm) were calculated for each rat. Statistical significance was determined using a 1×4 analysis of variance, and Tukey tests were used for post hoc paired comparisons. The significance level was set at p=0.05.

Light microscopic examination of Golgi-impregnated tissues revealed reliable and consistent staining throughout the hippocampus in the 4 brains from each treatment group. CA1 pyramidal cells were always well represented and easily identifiable in the hippocampi of these brains. The mean (±SEM) apical dendrite spine densities of pyramidal cells in the CA1 region of the hippocampus are depicted in FIG. 1.

Quantitative analysis of CA1 pyramidal cells revealed significant differences between treatment groups in the density of apical dendritic spines ($F[3,12]=10.65$, $p=0.001$). Control animals had significantly fewer apical dendritic spines in the CA1 region than treated animals (all $p's \leq 0.05$). There were no differences in dendritic spine density among treatment groups (all $p's > 0.10$).

The results obtained from these studies demonstrate that 17α-dihydroequilenin has protective effects on hippocampal CA1 region dendritic spines, an area of the brain known to be involved with cognitive functions such as memory. Since the CA1 region of the hippocampus has been linked to human anterograde memory, and CA1 pyramidal cell dendritic spines have been shown to be altered in senile dementia of the Alzheimer type [see Woolley, Catherine et al., *J. Comp. Neurol.* 336:293 (1993)], 17α-dihydroequilenin may indeed exert beneficial effects on the cognitive functions of the central nervous system.

Additionally, other physiological effects of 17α-dihydroequilenin make this potential pharmaceutical agent far superior for use in the prevention and treatment of estrogen deficiency related neurodegeneration and cognitive dysfunction than other ERTs and hormone replacement therapies. In this regard, 17α-dihydroequilenin does not cause hyperplasia in uteri or mammary glands of ovariectomized rats and nonhuman primates as demonstrated by one of the co-inventors of the present invention [see Washburn et al., supra, (1993) and Washburn et al., supra, (1996), respectively]. Since there is no uterotrophic effect, opposing progestins are unnecessary, thus mitigating the possibility of iatrogenic vaginal bleeding or increases in endometrial or breast neoplasia which are a concern with 17β-estradiol.

17α-dihydroequilenin also appears to have beneficial effects on the cardiovascular system, including improvement in cholesterol concentrations in ovariectomized rats [see Washburn et al., supra, (1993)], and prevention of abnormal acetylcholine-induced coronary vasoconstriction in both female and male nonhuman primates [see Washburn et al., supra, (1996)]. In addition, male nonhuman primates responded to 17α-dihydroequilenin with reduced levels of arterial low density lipoprotein accumulation and no effect on prostatic or testicular weight [see Washburn et al., supra, (1996)]. 17α-dihydroequilenin may also have beneficial effects on bone (see U.S. Pat. No. 5,545,635).

EXAMPLE 4

When 17α-dihydroequilenin is used in accordance with the present invention, it can be formulated into normal dosage forms such as capsules, tablets, powders, suspensions, emulsions, solutions, syrups, aerosols, soft and hard gelatin capsules, suppositories, injectable solutions and the like. 17α-dihydroequilenin can be administered by itself or in combination with pharmaceutically acceptable carriers, diluents, stabilizers, solubilizers, lubricants, binders and the like or excipients thereof. Regardless of the pharmaceutical formulation, 17α-dihydroequilenin will be found in a proportion that will impart the desired activity to the mammal.

17α-dihydroequilenin may also be injected parenterally, in which case it is administered in the form of a sterile solution containing other components such as glucose or saline. It is further contemplated that 17α-dihydroequilenin may be administered transdermally with the use of a transdermal patch containing the active ingredient, 17α-dihydroequilenin, and a pharmaceutical carrier. The transdermal patch allows the delivery of 17α-dihydroequilenin to the skin for systemic absorption into the blood stream.

The dosage requirements for 17α-dihydroequilenin for administration to patients will be based upon dosage requirements to achieve benefits for central nervous system, cardiovascular and bone protection. Dodge et al. [Abstract of presentation at the 10th International Congress of Endocrinology and The Endocrine Society, Jun. 12-15, 1996, San Francisco, Calif.] have demonstrated a wide therapeutic window which enables bone and cardiovascular protection (approximately 0.1 to about 1.0 mg/kg/day in rats) and uterine stimulation (approximately 6.0 mg/kg). The central nervous system protective dose in the present invention was about 0.625 mg/kg/day, and falls well within the therapeutic window disclosed by Dodge et al. Accordingly, it is believed that metabolically equivalent doses in men and women to those tested in both rats and non-human primates will achieve similar beneficial effects without any adverse effects on the uterus, breast, prostate and testes. Individualization of doses to achieve maximum benefit will be easily accomplished within the wide (five fold dose differential) therapeutic window separating the beneficial and adverse effects.

Of course, precise dosages for any form of administration to the patient will be determined by the administering physician based on their experience with the patient being treated. Generally, 17α-dihydroequilenin should be administered at a concentration that will achieve the desired result without causing any harmful or deleterious side effects. While it is contemplated that 17α-dihydroequilenin has demonstrated potential as a single agent therapeutic regimen, it is contemplated that this compound may be combined with another hormonal compound to enhance the overall beneficial effects of 17α-dihydroequilenin.

In view of the foregoing, 17α-dihydroequilenin appears to prevent the deleterious effects of hypoestrogenism on the central nervous, cardiovascular and skeletal systems without trophic effects on the uterus, endometrium or breast. Its target-tissue specificity suggests that 17α-dihydroequilenin has a great deal of potential as a single-agent therapeutic regimen for hormone replacement therapy in women suffering from estrogen deficiency conditions and/or diseases such as menopause. Additionally, those individuals, both males and females, at risk for cognitive dysfunction would likely benefit from a prophylactic administration of 17α-dihydroequilenin in accordance with the methods of the present invention.

All references referred to herein are hereby incorporated by reference in their entirety.

It should be understood that various changes and modifications to the presently preferred embodiments described herein will be apparent to those skilled in the art. By way of example, central nervous system protection by 17α-dihydroequilenin may enhance balance in elderly individuals, thereby reducing falls and preventing hip and other fractures.

Such changes and modifications can be made without departing from the spirit and scope of the present invention and without diminishing its attendant advantages. It is therefore intended that such changes and modifications be covered by the appended claims.

We claim:

1. A method of preventing estrogen deficiency related neurodegeneration and cognitive dysfunction in a mammal, comprising administering to a mammal susceptible to estrogen deficiency related neurodegeneration a therapeutically effective amount of 17α-dihydroequilenin or a mammalian metabolic conjugate thereof.

2. The method according to claim 1, wherein the route of administration for 17α-dihydroequilenin is selected from the group consisting of oral, intravenous, parental, transdermal, rectal, intravaginal, intranasal, and intrabronchial administration.

3. The method according to claim 1, wherein the administered compound is 17α-dihydroequilenin sulfate.

4. The method according to claim 1, wherein the mammal is a postmenopausal female.

5. The method according to claim 1, wherein the estrogen deficiency is menopause related.

6. The method according to claim 1, wherein the estrogen deficiency includes premature ovarian failure, anorexia/bulemia, amenorrhea resulting from physical or mental stress, genetic absence of ovaries, and surgical or chemical castration.

7. A method of treating estrogen deficiency related neurodegeneration and cognitive dysfunction in a mammal, comprising administering to an estrogen deficient mammal in need of increased cognitive function a therapeutically effective amount of 17α-dihydroequilenin or a mammalian metabolic conjugate thereof.

8. The method according to claim 7, wherein the route of administration for 17α-dihydroequilenin is selected from the group consisting of oral, intravenous, parental, transdermal, rectal, intravaginal, intranasal, and intrabronchial administration.

9. The method according to claim 7, wherein the administered compound is 17α-dihydroequilenin sulfate.

10. The method according to claim 7, wherein the estrogen deficiency is menopause related.

11. A method of preventing neurodegeneration and cognitive dysfunction associated with Alzheimer's disease and other dementia related disorders, comprising administering to a mammal susceptible to neurodegeneration associated with Alzheimer's disease or other dementia related disorders a therapeutically effective amount of 17α-dihydroequilenin or a mammalian metabolic conjugate thereof.

12. The method according to claim 11, wherein the route of administration for 17α-dihydroequilenin is selected from the group consisting of oral, intravenous, parental, transdermal, rectal, intravaginal, intranasal, and intrabronchial administration.

13. The method according to claim 11, wherein the administered compound is 17α-dihydroequilenin sulfate.

14. The method according to claim 11, wherein the mammal includes males and females.

15. The method according to claim 14, wherein the females are postmenopausal.

16. A method of preventing atrophy of hippocampal dendritic spine density associated with estrogen-deficiency diseases and/or conditions, comprising administering to a mammal susceptible to estrogen deficiency diseases and/or conditions a therapeutically effective amount of 17α-dihydroequilenin or a mammalian metabolic conjugate thereof.

17. The method according to claim 16, wherein the route of administration for 17α-dihydroequilenin is selected from the group consisting of oral, intravenous, parental, transdermal, rectal, intravaginal, intranasal, and intrabronchial administration.

18. The method according to claim 16, wherein the administered compound is 17α-dihydroequilenin sulfate.

19. The method according to claim 16, wherein the mammal is a postmenopausal female.

20. The method according to claim 16, wherein the estrogen deficiency diseases and/or conditions include premature ovarian failure, anorexia/bulemia, amenorrhea resulting from physical or mental stress, genetic absence of ovaries, and surgical or chemical castration.

21. A method of preventing atrophy of hippocampal dendritic spine density associated with Alzheimer's disease and other dementia related disorders, comprising administering to a mammal susceptible to neurodegeneration associated with Alzheimer's disease or other dementia related disorders a therapeutically effective amount of 17α-dihydroequilenin or a mammalian metabolic conjugate thereof.

22. The method according to claim 21, wherein the route of administration for 17α-dihydroequilenin is selected from the group consisting of oral, intravenous, parental, transdermal, rectal, intravaginal, intranasal, and intrabronchial administration.

23. The method according to claim 21, wherein the mammal includes males and females.

24. The method according to claim 23, wherein the females are postmenopausal.

* * * * *